United States Patent [19]
Von Oepen

[11] Patent Number: 6,048,361
[45] Date of Patent: Apr. 11, 2000

[54] BALLOON CATHETER AND MULTI-GUIDEWIRE STENT FOR IMPLANTING IN THE REGION OF BRANCHED VESSELS

[75] Inventor: Randolf Von Oepen, Hirrlingen, Germany

[73] Assignee: Jomed Implantate GmbH, Rangendingen, Germany

[21] Appl. No.: 09/078,956

[22] Filed: May 14, 1998

[30] Foreign Application Priority Data

May 17, 1997 [DE] Germany ............... 297 08 803 U

[51] Int. Cl.⁷ ..................... A61F 2/06; A61B 17/32
[52] U.S. Cl. ............... 623/1; 606/108; 606/198
[58] Field of Search ............ 623/1, 12; 604/96, 604/102; 606/198, 108

[56] References Cited

U.S. PATENT DOCUMENTS

| | | | |
|---|---|---|---|
| 4,856,516 | 8/1989 | Hillstead | 604/104 |
| 4,994,071 | 2/1991 | MacGregor | |
| 5,304,132 | 4/1994 | Jang | 604/96 |
| 5,609,627 | 3/1997 | Goicoechea et al. | |
| 5,723,004 | 3/1998 | Dereume et al. | 623/1 |
| 5,800,393 | 9/1998 | Sahota | 604/96 |
| 5,807,404 | 9/1998 | Richter | 623/1 |
| 5,836,964 | 11/1998 | Richter et al. | 606/194 |
| 5,855,600 | 1/1999 | Alt | 623/1 |
| 5,868,783 | 2/1999 | Tower | 606/198 |
| 5,893,887 | 4/1999 | Jayaraman | 623/1 |
| 5,895,402 | 4/1999 | Hundertmark | 606/171 |
| 5,916,194 | 6/1999 | Jacobsen et al. | 604/96 |

FOREIGN PATENT DOCUMENTS

| | | | |
|---|---|---|---|
| 29701758 | 2/1997 | European Pat. Off. | 623/1 |
| 297 01 758 U | 3/1997 | Germany . | |
| 297 01 758 U1 | 5/1997 | Germany . | |

*Primary Examiner*—David H. Willse
*Assistant Examiner*—Suzette J. Jackson
*Attorney, Agent, or Firm*—Michael J. Striker

[57] ABSTRACT

A device for implanting into a body vessel in the region of a vessel branching has a radially expandable stent formed as a hollow cylindrical element and provided with an increased radial opening, and a balloon catheter on which the stent is pre-mounted for implanting in the vessel, the balloon catheter having a hollow chamber for passage of a guiding wire so that it exits in a center of the increased opening from the hollow chamber and the stent.

13 Claims, 3 Drawing Sheets

BALLOON CATHETER AND MULTI-GUIDEWIRE STENT FOR IMPLANTING IN THE REGION OF BRANCHED VESSELS

BACKGROUND OF THE INVENTION

The present invention relates to a radially expandable stent for implanting in a body vessel in the region of a vessel branch, formed as a hollow-cylindrical element.

Radially expandable stents of the above mentioned general type are known in the art. The radial expandable stents are utilized at narrow locations in body vessels or body hollows for expanding the narrowing and stabilizing the vessel wall. Such narrowings of the body vessels can occur in the region of vessel branches. The use of a conventional stent is not possible here, since its wall would prevent a free blood circulation in the branched vessel. The German patent document DE 297 01 758.6 discloses a special stent which has a portion with increased radial openings so that this portion can extend over the branch location of the side branch vessel and no longer prevents the blood passage or hinders it only insignificantly. In the case of corresponding unfavorable stenosis formation of the main vessel directly in the branching region this stent however can not sufficiently cover the sickened vessel portion due to great radial openings extending over a whole portion.

SUMMARY OF THE INVENTION

Accordingly, it is an object of the present invention to provide a radially expandable stent for implanting in a body vessel in the region of a vessel branch, which avoids the disadvantages of the prior art.

In keeping with these objects and with others which will become apparent hereinafter, one feature of present invention resides, briefly stated, in a radially expandable stent which has an increased radial opening and is premountable for implanting in the vessel on a balloon catheter, wherein the balloon catheter has a hollow chamber for passage of a guiding wire which extends in a center of the increased opening out of the hollow chamber and the stent.

Due to an increased opening in the stent wall, which can be located directly over the branching location, it is ensured that the total vessel wall is reliably protected by the stent. The increased opening has the purpose of guaranteeing the unobjectionable blood flow in the side branch vessel.

For accurate positioning of the stent however corresponding auxiliary means is needed. With the utilization of x-ray contrast means, the exact positioning of an increased opening over the branch is not possible. Therefore, the inventive stent is premounted on a balloon catheter which has a hollow chamber for a guiding wire exiting through the increases opening. With the help of the guiding wire it is possible to position the great opening of the stent exactly over the exit of the side vessel. For this purpose, the catheter, by turning and displacing with the help of x-ray contrast means and visual monitoring on the x-ray screen, is manipulated until it is possible to introduce the second guide wire in the side branch vessel.

For insertion of the balloon catheter into the main vessel, the balloon catheter can be provided in a known manner with a hollow chamber extending along its longitudinal axis for a first guide wire exiting at the tip of the balloon catheter. It can be displaced along the guide wire without problems up to the vessel branch, before the use of the second guide wire for exact positioning of the increased opening. It is guaranteed that the catheter is exactly positioned, and then the balloon is inflated, and the stent is located on the vessel wall. Finally, the catheter can be pulled along the both guide wires from the vessel. The stent remains with the both wires in the vessel.

Via the guide wire of the side branch vessel a further balloon catheter can be inserted into the branch for further expansion around the increased opening. Thereby it can be guaranteed that no wall part of the stent hinders the blood flow in the side branch vessel.

For forming the balloon catheter, various possibilities can be acceptable. For example, the hollow chamber for the guide wire which is guided from the increased opening can be formed by mounting a pipe on the balloon surface. This hollow chamber can be also formed by an intermediate space of a double-walled balloon. Also coating of a stretchable hose piece up to the balloon is possible, to provide a hollow chamber between this coated hose piece and the balloon for the guiding wire.

In an alternative embodiment, the balloon catheter can include three coaxially arranged hoses. Both inwardly located hoses can form a hollow chamber for receiving the both guiding wires.

The stent itself can be formed in different ways. It can have a multi-cellular wall and can be produced of a pipe. However, the stent can be also formed as a wire. In this case, it can be bent, twisted, knitted or textured from the wire. Advantageously, the increased opening is arranged in the center of the stent. However, also an eccentric arrangement of the increased opening can be realized for various applications.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1C:
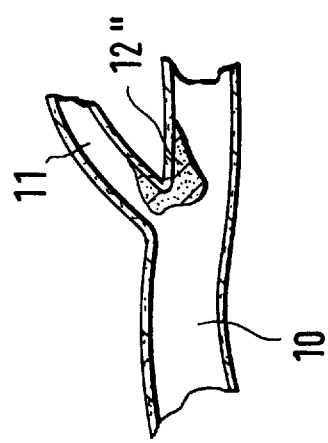
FIG. 1 is a schematic view showing three vessel branches with stenosis.
Figure 1B:
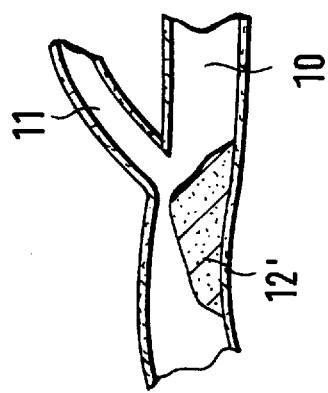
Figure 1A:
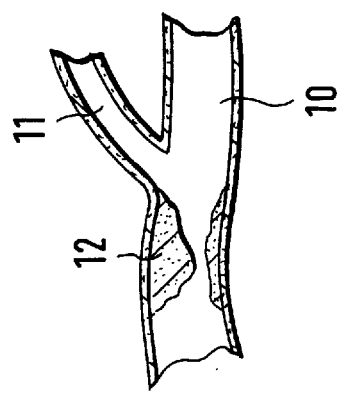

FIGS. 1a, 1b, 1c show three examples of typical stenoses which can occur in vessel branches. FIG. 1a shows the stenosis 12 in a main vessel 10 before branching of a side branch vessel 11. In FIG. 1b a very great stenosis 12' is located directly opposite to the branching of the side branch vessel 11. In FIG. 1c it is located in a transition between the main vessel 10 and the side branch vessel 11.

Figure 2:
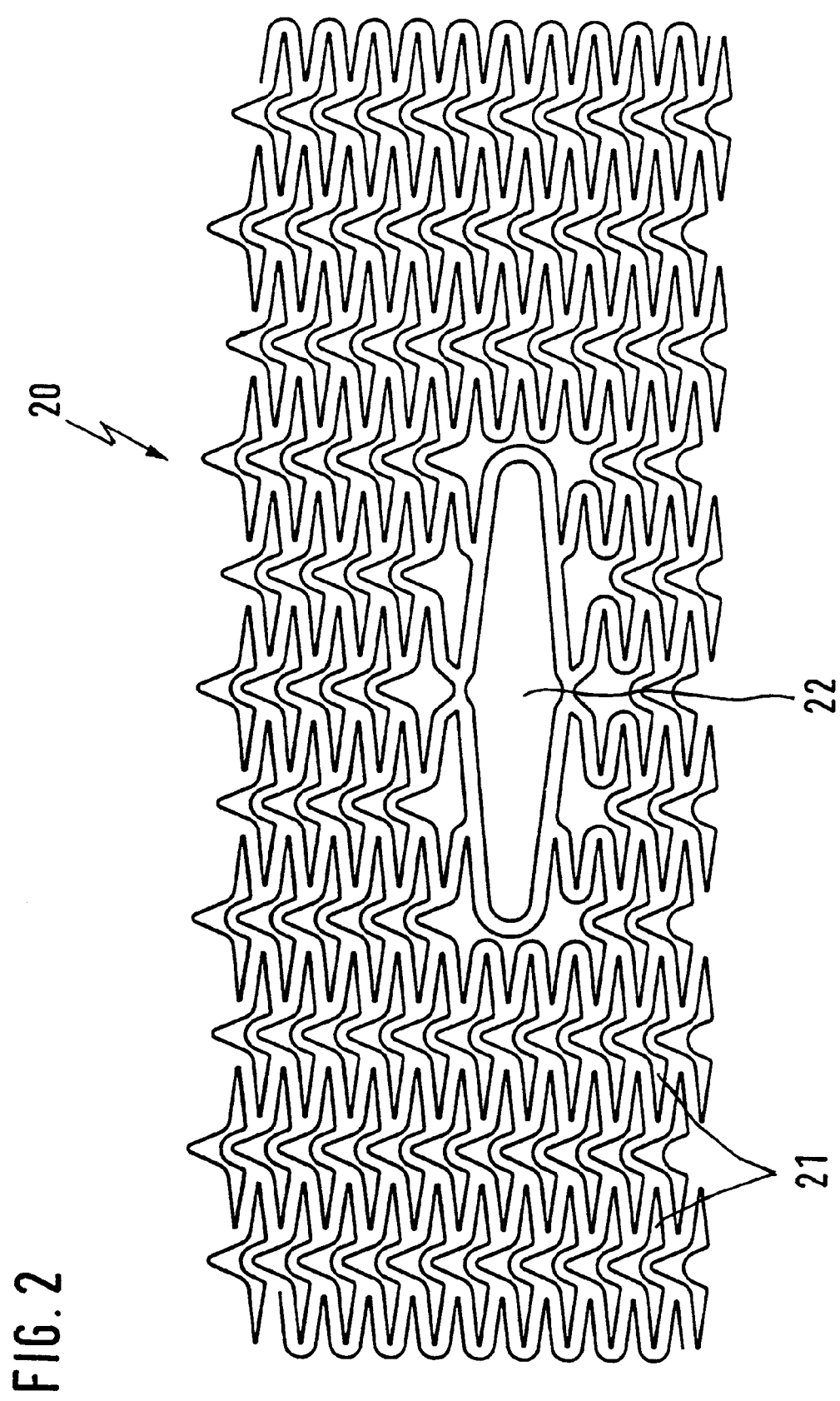
FIG. 2 is a view showing a surface structure of a stent in accordance with the present invention.
Figure 3:
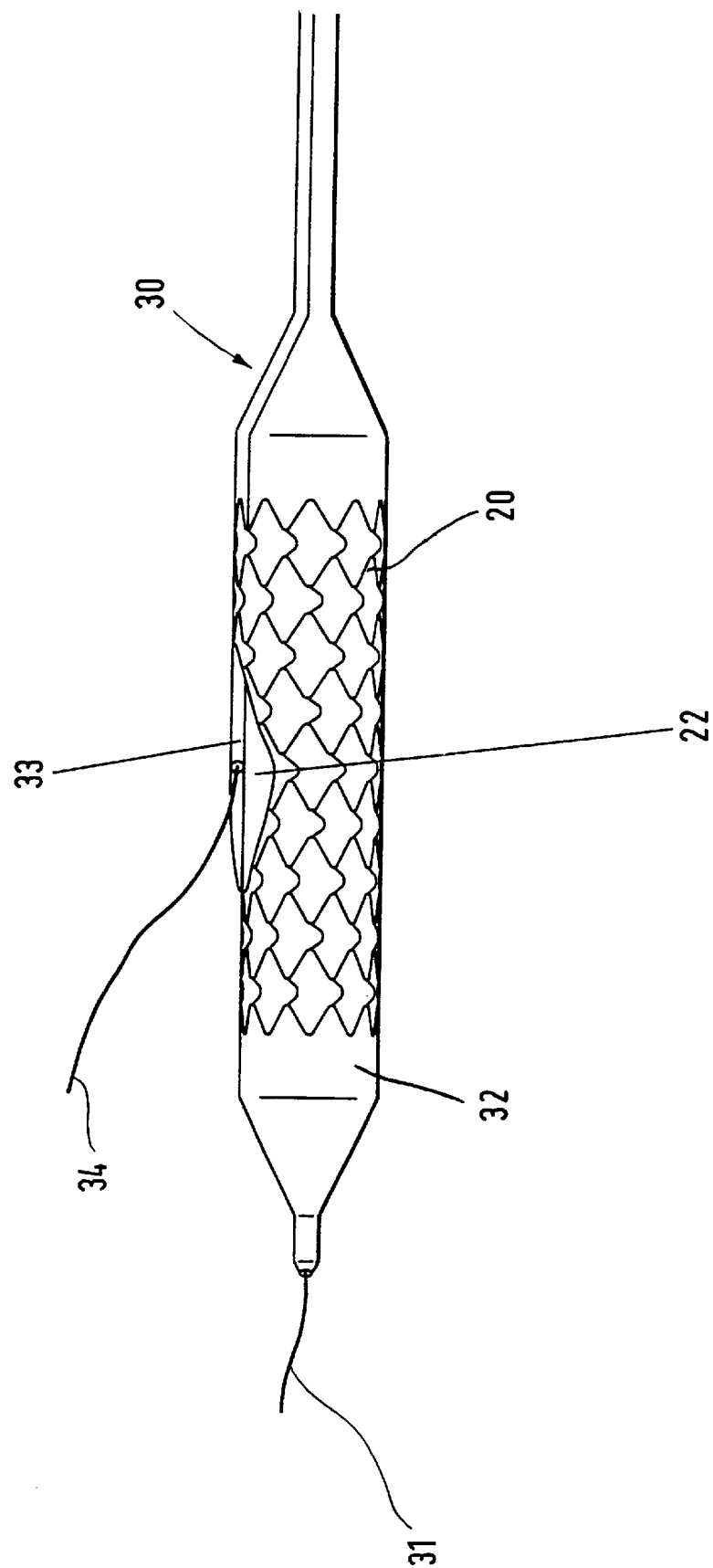
FIG. 3 is a side view of a stent premounted on a balloon catheter.

In particular the stenosis shown in FIG. 1b is covered only insufficiently with a bifurcation stent with a portion having increased radial openings. Exactly for such a case, the inventive stent can be suitable, as shown in FIGS. 2 and 3. FIG. 2 shows the surface structure of a stent 20 which has a plurality of diamond-shaped radial opening 21 in stretch condition. A single, very large diamond-shape openings 22 is formed in the central region of the stent 20. The opening 22 can be located in a body vessel exactly over the branching of a side branch vessel 11 shown in FIG. 1.

In order to make possible the position-accurate placing of the stent 20, it is premounted on a balloon catheter 30 as shown in FIG. 3. The balloon catheter 30 as shown in FIG. 3 has a hollow chamber formed in its interior and not shown in detail. A first guiding wire 31 passes through the hollow chamber of the balloon catheter 30. The stent 20 is pulled on the catheter 30 in the region of a balloon 32. A further hollow chamber 33 extends in the region of the balloon 32 for passing a second guiding wire 34. In the region of the increased opening 22 the second guiding wire 34 exits from the hollow chamber 33 and from the stent 20. The guiding wire 34 is inserted in a side branch vessel 11 and serves as an adjusting aid for the positioning of the stent 20 in a body vessel 10. After pulling of the balloon catheter 30 from the vessel 10 it can also serve as a guiding wire for a further balloon catheter for expanding of the increased opening 22.

The shown embodiments of the balloon catheter 30 as well as the stent 20 are however only exemplary. The required hollow chamber 33 for passage of the second guiding wire 34 can be formed for example by a double-walled balloon 32 or two coaxial hose pieces. The shown stent 20 is cut from a tube. However, it can be also bent, knitted, twisted or structured from a wire.

It will be understood that each of the elements described above, or two or more together, may also find a useful application in other types of constructions differing from the types described above.

While the invention has been illustrated and described as embodied in radially expandable stent for implanting In a body vessel in the region of a vessel branch, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for implanting a body vessel in the region of a vessel branching, comprising a radially expandable stent formed as a hollow cylindrical element and provided with an increased radial opening; and a balloon catheter on which said stent is premounted for implanting in the vessel, said balloon catheter having a hollow chamber for passage of a guiding wire so that it exits in a center of said increased opening from said hollow chamber and said stent, said balloon catheter being provided with another longitudinal chamber extending along a longitudinal axis of said catheter and formed so that a further guiding wire extends through said other longitudinal chamber and exits at a tip of said balloon catheter.

2. A device as defined in claim 1, wherein said stent is dilatable so that after a dilation of said stent, said balloon catheter is pullable along said guiding wires out of the vessel.

3. A device as defined in claim 1, wherein said further guiding wire is guided through said other hollow chamber out of said increased opening.

4. A device as defined in claim 3, wherein said balloon catheter has a balloon portion, said other hollow chamber for said further guiding wire guided out of said increased opening being formed by a pipe mounted on an outer surface of said balloon portion of said catheter.

5. A device as defined in claim 3, wherein said catheter has a balloon portion which is formed as a double-walled balloon, said other hollow chamber for guiding said further wire from said increase opening being formed as an intermediate chamber of said double-wall balloon.

6. A device as defined in claim 3, wherein said balloon catheter has a balloon portion, said other hollow chamber for guiding said further wire out of said increased opening being formed as an intermediate chamber between said balloon portion and a stretchable hose piece which is pulled onto said balloon portion.

7. A device as defined in claim 1, wherein said balloon catheter is composed of three coaxial hoses arranged so that two inwardly located hoses form said hollow chambers for receiving said guiding wires.

8. A device as defined in claim 1, wherein said stent is composed of a pipe and has a multi-cellular wall.

9. A device as defined in claim 1, wherein said stent is bent from a wire.

10. A device as defined in claim 1, wherein said stent is formed as a wire selected from the group consisting of structured wire, knitted wire and twisted wire.

11. A device as defined in claim 1, wherein said increased opening is arranged in a center of said stent.

12. A device as defined in claim 1, wherein said increased opening is arranged eccentrically on said stent.

13. A device for implanting into a body vessel in the region of a vessel branching, comprising a radially expandable stent formed as a hollow cylindrical element and provided with an increased radial opening; a balloon catheter on which said stent is pre-mounted for implanting in the vessel, said balloon catheter having a first hollow chamber and another longitudinal chamber extending along a longitudinal axis of said catheter; and guiding means including a first guiding wire passing through said first hollow chamber so that it exits in a center of said increased opening from said hollow chamber and said stent, and a further guiding wire extending through said other longitudinal chamber and exiting at a tip of said balloon catheter.

* * * * *